(12) United States Patent
Saunders et al.

(10) Patent No.: US 8,295,906 B2
(45) Date of Patent: Oct. 23, 2012

(54) MRI GUIDED RADIATION THERAPY

(75) Inventors: John K. Saunders, Manitoba (CA); David Graves, Manitoba (CA); Gordon Scarth, Manitoba (CA)

(73) Assignee: Imris Inc, Winnipeg, MB (CA)

( * ) Notice: Subject to any disclaimer, the term of this patent is extended or adjusted under 35 U.S.C. 154(b) by 470 days.

(21) Appl. No.: 12/194,963

(22) Filed: Aug. 20, 2008

(65) Prior Publication Data

US 2010/0049030 A1 Feb. 25, 2010

(51) Int. Cl.
*A61B 5/055* (2006.01)

(52) U.S. Cl. .................................... 600/411

(58) Field of Classification Search .......... 600/410, 600/411, 413, 415, 428
See application file for complete search history.

(56) References Cited

U.S. PATENT DOCUMENTS

| | | | |
|---|---|---|---|
| 5,178,146 A | 1/1993 | Giese | |
| 5,402,783 A | 4/1995 | Friedman | |
| 5,537,452 A | 7/1996 | Shepherd | |
| 5,735,278 A | 4/1998 | Hoult et al. | |
| 5,800,353 A | 9/1998 | McLaurin | |
| 6,198,957 B1 | 3/2001 | Green | |
| 6,725,078 B2 | 4/2004 | Bucholz et al. | |
| 6,731,970 B2 | 5/2004 | Schlossbauer et al. | |
| 6,898,456 B2 | 5/2005 | Erbel | |
| 7,265,356 B2 | 9/2007 | Pelizzari | |
| 7,356,112 B2 | 4/2008 | Brown | |
| 2007/0153969 A1* | 7/2007 | Maschke | 378/4 |

* cited by examiner

*Primary Examiner* — Michael Rozanski

(74) *Attorney, Agent, or Firm* — Adrian D. Battison; Ade & Company Inc.

(57) ABSTRACT

Radiation therapy of a lesion within a patient is guided to take into account movement of the lesion caused by respiration and/or cardiac effects by using MRI to image the patient while on the treatment support to obtain a series of images of a location of the lesion within the patient while obtaining data relating to respiration and/or cardiac function of the patient to generate lesion movement data as a function of respiration and/or cardiac function. After the magnet is removed from the bunker, during the radiation therapy, real time data relating to respiration and/or cardiac function of the patient is used to guide the radiation therapy using the lesion movement data obtained during the imaging.

8 Claims, 2 Drawing Sheets

MRI GUIDED RADIATION THERAPY

BACKGROUND OF THE INVENTION

A radiotherapy device generally includes a linear electron beam accelerator which is mounted on a gantry and which can rotate about an axis which is generally parallel to the patient lying on the patient couch. During the radiation therapy, the patient is treated using either an electron beam or an X-Ray beam produced from the original electron beam. The electron or X-Ray beam is focused at a target volume in the patient by the combination of the use of a collimator and the rotation of the beam. The patient is placed on a couch which can be positioned such that the target lesion can be located in the plane of the electron beam as the gantry rotates in two directions.

The objective of the radiation therapy is to target the lesion with a high dose of radiation over time and to have minimal impact on all the surrounding normal tissue. The first task is to precisely locate the tumor in three dimensional space. The best technique for this is MRI since this technology provides high resolution in the imaging of soft tissue to provide high soft tissue contrast.

Even though MRI provides good location of the tumor at the time of the measurement, these images are normally recorded two to three days prior to the treatment and so may not be completely representative of tumor location on the day of treatment. This is because the movement of the patient over time can cause the anatomical location of the tumor to move. The oncologists therefore tend to increase the target volume to be certain that all of the tumor tissue receives the required dose of the radiation, even though this increase in the volume of the tissue exposed to radiation also necessarily targets healthy tissue with consequential damage to the healthy tissue. The expectation is that all cells in the targeted region will be killed and this includes both the lesion and the healthy tissue. This produces collateral damage and may have a significant impact of the quality of life of the patient.

An additional challenge to effective radiation treatment is the effect of motion of the tumor in the body due to respiratory and cardiac motion. This results in tumor masses moving making the continuous accurate targeting for treatment difficult. Again therefore the oncologists generally increase the size of the target volume radiated to accommodate movement of the lesion during respiratory and cardiac movement.

A number of attempts have been made to improve the accuracy of the location of the lesion for radiotherapy.

U.S. Pat. No. 5,178,146 (Giese) issued Jan. 12, 1993 discloses a grid system of contrast material which is compatible with MRI which is used to plan radiotherapy.

The following patents disclose a technique for identifying the target volume using MRI which is used to plan radiotherapy;

U.S. Pat. No. 5,402,783 (Friedman) assigned to Eco-Safe and issued Apr. 4, 1995;

U.S. Pat. No. 5,537,452 (Shepherd) issued Jul. 16, 1996;

U.S. Pat. No. 5,800,353 (McLaurin) issued Sep. 1, 1998;

U.S. Pat. No. 6,198,957 (Green) assigned to Varian and issued Mar. 6, 2001;

A number of attempts have been made to compensate for the movement of the lesion during the irradiation.

U.S. Pat. No. 6,725,078 (Bucholz) assigned to St Louis University and issued Mar. 6, 2001 discloses a combined MRI and radiotherapy system which operate simultaneously but without interference so that the location of the lesion can be tracked during the radiotherapy.

U.S. Pat. No. 6,731,970 (Schlossbanner) assigned to BrainLab and issued May 4, 2004 discloses a method for breath compensation in radiation therapy, where the movement of the target volume inside the patient is detected and tracked in real time during radiation by a movement detector. The tracking is done using implanted markers and ultrasound.

U.S. Pat. No. 6,898,456 (Erbel) assigned to BrainLab and issued May 24, 2005 discloses method for determining the filling of a lung, wherein the movement of an anatomical structure which moves with breathing, or one or more points on the moving anatomical structure whose movement trajectory is highly correlated with lung filling, is detected with respect to the location of at least one anatomical structure which is not spatially affected by breathing, and wherein each distance between the structures is assigned a particular lung filling value. There is also disclosed a method for assisting in radiotherapy during movement of the radiation target due to breathing, wherein the association of lung filling values with the distance of the moving structure which is identifiable in an x-ray image and the structure which is not spatially affected by breathing is determined, the current position of the radiation target is detected on the basis of the lung filling value, and wherein radiation exposure is carried out, assisted by the known current position of the radiation target.

U.S. Pat. No. 7,265,356 (Pelizzari) assigned to University of Chicago and issued Sep. 4, 2007 discloses an image-guided radiotherapy apparatus and method in which a radiotherapy radiation source and a gamma ray photon imaging device are positioned with respect to a patient area so that a patient can be treated by a beam emitted from the radiotherapy apparatus and can have images taken by the gamma ray photon imaging device. Radiotherapy treatment and imaging can be performed substantially simultaneously and/or can be performed without moving the patient in some embodiments.

U.S. Pat. No. 7,356,112 (Brown) assigned to Elektra and issued April 8, 2008 discloses that artifacts in the reconstructed volume data of cone beam CT systems can be removed by the application of respiration correlation techniques to the acquired projection images. To achieve this, the phase of the patients breathing is monitored while acquiring projection images continuously. On completion of the acquisition, projection images that have comparable breathing phases can be selected from the complete set, and these are used to reconstruct the volume data using similar techniques to those of conventional CT. This feature in the projection images can be used to control delivery of therapeutic radiation dependent on the patient's breathing cycle, to ensure that the tumor is in the correct position when the radiation is delivered.

The same company Elektra AB of Stockholm Sweden, as set out in an undated page taken from their web site, have developed a machine using CT guided radiation where CT is used to image the patient just prior to irradiation. They state that better margins can be set using Motion View sequential imaging.

There are previous proposals for using MRI magnets to monitor treatment using electron beams created by a linear accelerator. The problem with this is the non-compatibility of linear accelerators and MRI. This arises because the magnetic field generated by the magnet of course interferes with the operation of the linear accelerator to an extent which cannot be readily overcome. It has however been found that relatively low field MRI units can be used with gamma radiation produced from cobalt −60.

In U.S. Pat. No. 5,735,278 (Houllt et al) issued Apr. 7, 1998, is disclosed a medical procedure where a magnet is movable relative to a patient and relative to other components of the system. The moving magnet system allows intra-operative MRI imaging to occur more easily in neurosurgery patients, and has additional applications for liver, breast, spine and cardiac surgery patients.

SUMMARY OF THE INVENTION

It is one object of the invention to provide a method for guiding radiation therapy which can accommodate movement of the lesion caused by respiration and/or cardiac motion.

According to one aspect of the invention there is provided a method for guiding radiation therapy of a patient comprising:

locating a patient on a treatment support, the patient having a lesion requiring radiation therapy;

preparing the patient for radiation therapy on the treatment support;

moving a magnet of an MRI system into a position at the treatment support for imaging the patient while on the treatment support;

while the patient is on the treatment support using the MRI system to obtain a series of images of a location of the lesion within the patient;

while the patient is on the treatment support, during the obtaining of the images, obtaining data relating to respiration and/or heartbeat of the patient;

using the series of images to generate lesion movement data relating to a correlation between movement of the location of the lesion and the data relating to the respiration and/or heartbeat;

moving the magnet of the MRI system away from the treatment support so as to allow the radiation therapy;

and during the radiation therapy, using real time data relating to respiration and/or heartbeat of the patient and guiding the radiation therapy using the lesion movement data correlated to the real time data of the respiration and/or heartbeat.

Preferably the images from the MR system in an MR coordinate system are correlated relative to a coordinate system of the radiation therapy by using the treatment support as a common baseline.

Preferably the magnet is an annular magnet surrounding a longitudinal axis and is moved longitudinally of its axis.

Preferably the radiation therapy is generated by a collimated radiation source which is rotated round the lesion, generally in conjunction with movement of the patient support, in a manner which controls the application of a required dose of radiation to the lesion while accommodating the shape of the lesion and the movement of the lesion.

Preferably the radiation therapy is provided by a radiation source where the radiation source and the treatment support are located in a room shielded to prevent release of the radiation and wherein the room includes a door through which the magnet moves to remove the magnet from the room during the therapy.

Preferably the lesion movement data relating to a correlation between movement of the location of the lesion and the data relating to the respiration and/or heartbeat is obtained during a plurality of respiration and/or heartbeat cycles.

Preferably the data relating to respiration of the patient is obtained by a sensor independent of the MRI system.

Preferably the data relating to respiration of the patient is obtained by a sensor responsive to movement of the chest of the patient, such as a simple chest attached monitor.

In order to accommodate different rates, and therefore depths, of breathing, the system can be arranged to monitor the movement of the lesion during different depths of breathing from maximum to minimum and to use the required pattern of movement for the breaths taken during the radiation therapy depending on the depth of breathing as determined by the monitor during the radiation therapy.

Interpolation can be used to generate some patterns of movement of the lesion between the maximum and minimum.

Alternatively and more preferably, the system acts to generate a pattern of movement of the lesion during a normal breathing pattern and heart rate pattern at a set rate comfortable to the patient and acts to monitor the respiratory and/or the cardiac cycles during radiation therapy beam application to ensure that the respiration rate and/or the cardiac rate has not changed outside of the bounds set for the needed accuracy of the movement of the beam. If the respiration rate or cardiac rate has changed by a sufficient degree, the radiation therapy beam is either halt, or alternatively paused until the respiratory rate and the cardiac rate can locked onto again, and match the rate detected during the MR data acquisition for accurate prediction of lesion movement.

The key feature is the ability to bring the MRI magnet into the radiation therapy room, image and retract the magnet. The radiation therapy unit is always stored in a bunker with thick concrete walls or lead walls so that no radiation escapes. A radiation system is now available which has doors which are of sufficient size and arrangement to allow the MRI system to enter and leave the radiation therapy room on rails. The radiation bunker itself is sufficient in size and arrangement to allow the MRI magnet to enter.

BRIEF DESCRIPTION OF THE DRAWINGS

One embodiment of the invention will now be described in conjunction with the accompanying drawings in which.

In the drawings like characters of reference indicate corresponding parts in the different figures.

DETAILED DESCRIPTION

Figure 1:
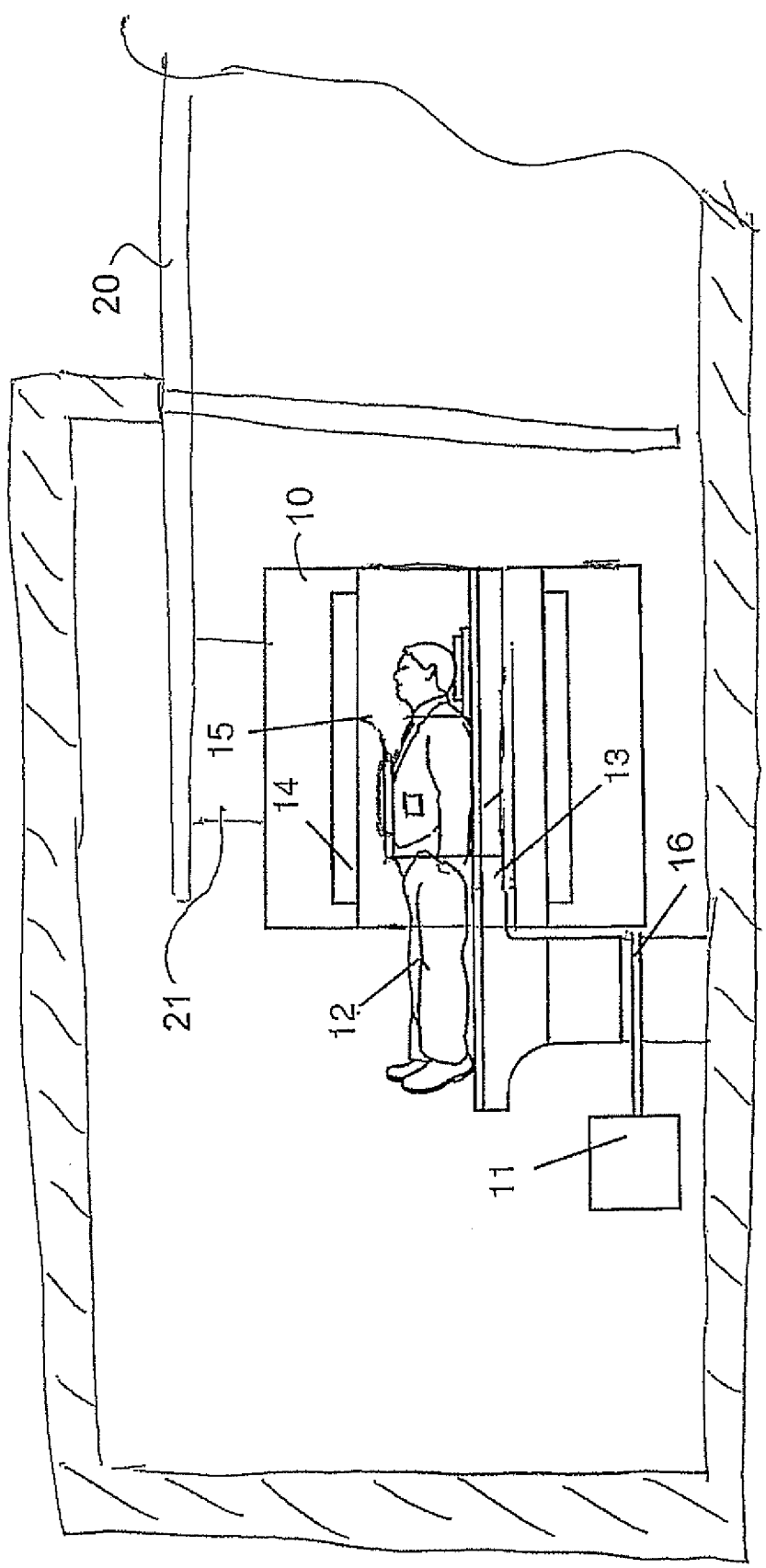
FIG. 1 is a schematic side elevation of a radiation therapy room into which a magnet of an MRI system has been moved for imaging.

In FIG. 1 is shown schematically a magnetic resonance imaging system which includes a magnet 10 having a bore 11 into which a patient 12 can be received on a patient table 13. The system further includes an RF transmit body coil 14 which generates a RF field within the bore.

The movable magnet is carried on a rail system 20 with a support 21 suspended on the rail system. Further details of this construction as available from published US application 2008/0038712 published Feb. 14, 2008 assigned to the present assignees, the disclosure of which is incorporated herein by reference.

The system further includes a receive coil system generally indicated at 15 which is located at the isocenter within the bore and receives signals generated from the human body in conventional manner. A RF control system acts to control the transmit body coil 14 and to receive the signals from the receive coil 15.

Figure 2:
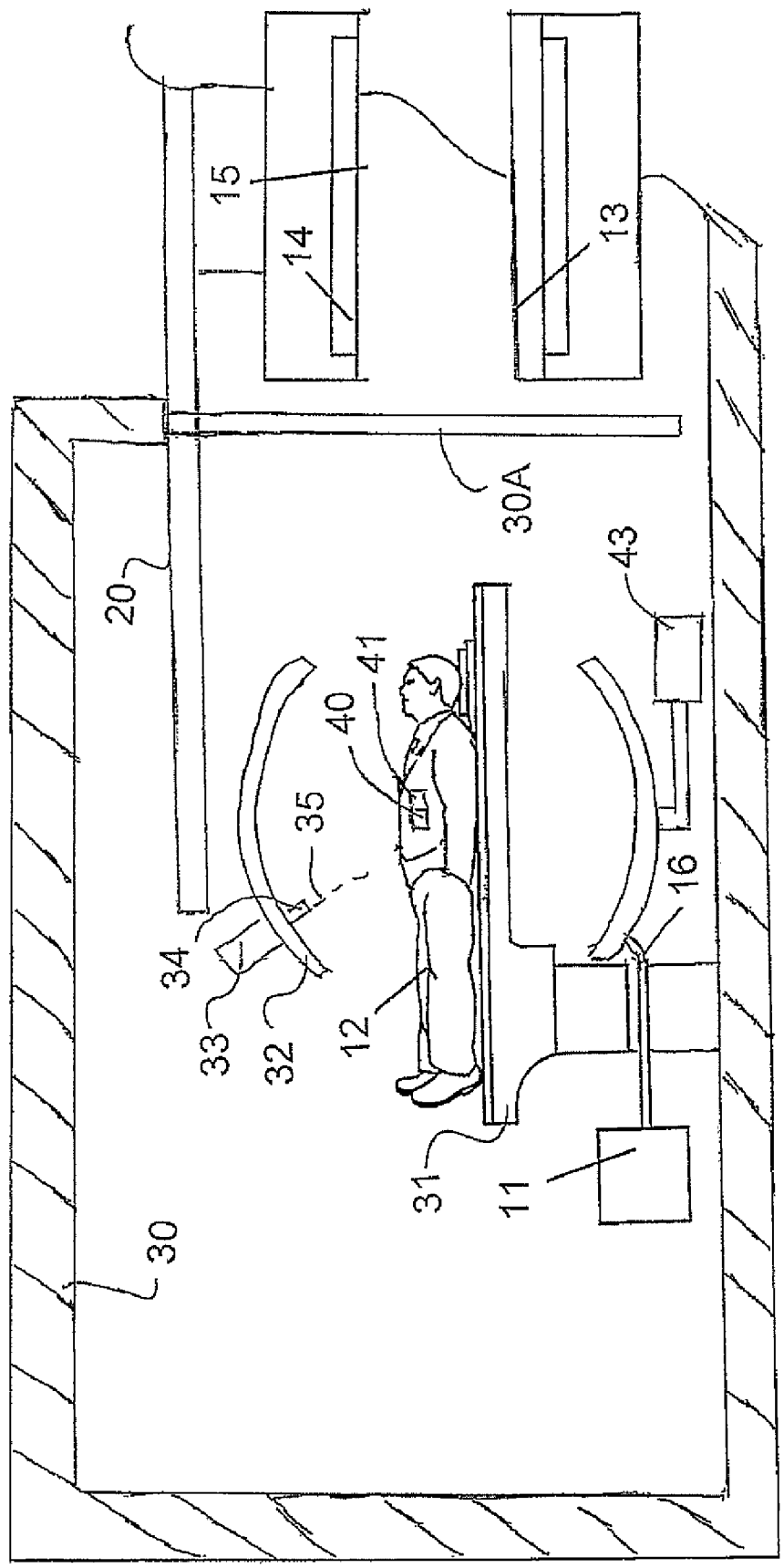
FIG. 2 is a schematic side elevation of the radiation therapy room of FIG. 1 from which the magnet of the MRI system has been removed after imaging.

The MRI system is used in conjunction with a patient radiation therapy system shown better in FIG. 2 with the magnet 10 of the MRI system removed. Thus the therapy system includes a bunker or room 30 within which is mounted a patient support 31 and a radiation gantry 32. The gantry carries a radiation source 33, which is in most cases a linear accelerator associated with a collimator 34 for generating a beam 35 of radiation. Systems are available for example from Siemens where the radiation system and the patient support are controlled to focus the beam onto any lesion of any shape within the patient body, bearing in mind complex shapes of lesion which are required to be radiated.

The patient having a lesion requiring radiation therapy is placed on the treatment support 31 and prepared for the radiation therapy on the treatment support.

During the initial imaging phase, the magnet of the MRI system is carried into the imaging position at the treatment support for imaging the patient while on the treatment support. The MRI system is used while the patient is on the treatment support to obtain a series of sequential high-speed images of the location of the lesion within the patient. This is done while obtaining data, using a simple respiration monitor system 40 and/or cardiac function monitor system 41, relating to respiration and/or cardiac function of the patient and the series of images are used to generate as set of lesion movement data relating to a correlation between movement of the location of the lesion and the data relating to the respiration and/or cardiac function. Thus the movement is plotted as a function of respiration and/or cardiac function data.

The magnet of the MRI system is then moved away from the treatment support through a door 30A of the bunker on the rails 20 so as to allow the radiation therapy to commence. During the radiation therapy, real time data relating to respiration of the patient is obtained by the sensor 40 and the radiation therapy is guided using the lesion movement data correlated to the real time respiration data.

Thus the patient is placed on the support or couch which can move such that the electron beam always irradiates the target volume. The gantry rotates such that the focus of the beam is always a relatively small volume. The table can move in three directions and this combined with the rotation focuses the treatment within a specified volume which is arranged o be as close as possible to the margins of the lesion in the patient. The goal is that this volume is the target lesion and only the target lesion. It is required that the entire target lesion receives the same maximum dose of radiation so that all cells within the targeted volume die. It is required that damage to adjacent normal tissue be minimal. Obviously, when the targeted lesion is moving the role of the MRI is to provide precise location of the lesion to that radiation unit so that it irradiates only tumor. This is accomplished by bringing the MRI system into the radiation room and placing the magnet over the patient on the patient couch. The patient couch is fully extended to reduce as much as possible the interaction between the magnet and the table. A number of MRI images are obtained rapidly as a function of time in the respiration cycle. The images need to be three dimensional ones since the irradiation is controlled in 3 dimensions. Once the images have been obtained, the magnet is retracted and treatment begins. The patient will continue to be monitored for respiration and it is this respiration that will drive the coordinates to the patient couch for the radiation treatment since the MRI images will provide the coordinates of the target lesion throughout the respiratory cycle.

The monitor 40 comprises an MR compatible respiratory cycle tracking device and the monitor 41 comprises an MR compatible cardiac cycle tracking device. The MR compatible respiratory and cardiac monitoring devices are capable of interfacing to the control system.

The radiation control unit 11 includes an electrical interface which allows control over its radiation beam over location and time. There is provided a boom system 43 to allow both the radiation unit to be moved sufficiently far from the magnet and moved into position for the radiation therapy.

A system is provided to generate a correlation between the coordinates systems of the patient that is the patient support table, the MR images, and the RT beam. The latter can be decomposed into the physical location of the radiation therapy unit relative to the patient support table, and the beam coordinate system relative to the radiation therapy unit.

The patient support table is MR compatible, and compatible with the magnet to allow imaging of the region between the head and lower abdomen.

The relative positions of the magnet and the patient support table must be controlled so that the Field of View (FOV) of the magnet is correctly positioned over the tissue to be radiated. This leads to two options, each differentiated by the success of shimming the magnet for imaging;

1. Position the magnet relative to a fixed-position patient support table with sufficient accuracy to align the FOV to the tissue to be radiated (shimming of the magnet not an issue).
2. Position the magnet to where it has been successfully shimmed, and then position a movable top portion of the patient support table (on a fixed patient support table pedestal) to align the FOV of the magnet to the tissue to be radiated.

The first method is preferred since it does not require movement of any part of the patient support table, but relies upon either the magnet to be successfully shimmed over some contiguous region in the bunker. The magnet can be moved manually until it reaches a pre-determined location, when it is stopped. The operator then instructs the system software to move the magnet into the optimal position for imaging based on the location of the tissue to be imaged. When the location is reached, the operator is informed that imaging can begin.

If the magnet cannot be successfully shimmed for imaging at the required locations, then an alternative method above is to move the table top on a fixed pedestal to align the magnet FOV. With this the movement is broken into two phases: move the magnet to the successful shim location, then move the table top. The magnet can be manually moved into the location where it was successfully shimmed, and then the operator instructs the system to move the table to the optimal position for imaging. When the table has reached this location, the operator is informed that imaging can begin.

There are 5 independent coordinate systems that must be correlated to map the MR imaging coordinate system into the radiation therapy unit coordinate system, using the patient support table coordinate system as the common baseline:

The Patient (and patient support table) coordinate system. This is the base of all coordinate systems.

The MR imaging coordinate system, relative to the magnet position.

The Magnet position, relative to the patient support table and patient radiation therapy unit relative to the patient support table and patient.

The radiation therapy beam relative to the radiation therapy unit.

The alignment the different coordinates systems to the patient support table occurs by aligning the MRI coordinate system to the magnet, then the magnet to the patient support table. This will allow the system to map the MR images to the coordinate system of the patient support table. The magnet can be aligned to the patient support table through on-site calibration. The feedback from the magnet mover to the system gives the position of the FOV to the images.

The radiation therapy unit can be aligned to the patient support table using markers on the patient support table that can be detected from a camera mounted co-adjacent to the radiation therapy unit. The camera is connected to the system to so that the physical position of the radiation therapy unit is known relative to the patient support table. The location of the radiation beam relative to the radiation therapy unit is assumed to be a constant, or known from vendor-supplied calibration that is available during installation of the system.

The MR compatible table allows imaging from the head to the lower abdominal region.

The system controller acts to analyze the imaging data provided by the MR console and control the radiation therapy unit in the following, the region of interest (ROI) is the anatomical region that is to be radiated.

The system software contains the following components:

A graphical user interface for display and control;

An interface to delineate the region of interest;

An interface for control of imaging acquisition from the MR console, including the imaging plain and a mechanism to start the imaging sequence (stop override functionality will also be provided);

An interface to display the 2D and 3D images, including the temporal view of the movement of the region of interest;

An interface to start the RT unit (stop override functionality will also be provided).

The software acts to analyze the temporal imaging data to detect the movement of the ROI and correlate to either to the respiratory cycle, the cardiac cycle, or both. Once the software has locked onto the periodic movement of the ROI, the image acquisition can automatically stop.

Using the periodic movement detected above, the system acts to map the temporal movement of the ROI to the required movement of the radiation therapy beam using the coordinate correlations discussed above.

During a radiation therapy session, the magnet is moved to the appropriate position for imaging of the anatomy to be radiated. Imaging occurs over a sufficient time to collect the necessary data capturing how the tissue to be radiated moves in relation to the respiratory and cardiac cycles, both of which are captured via separate and independent monitoring devices.

The system extracts the images from the MR console acquiring the images as the images are available, and analyzes the MR imaging temporal data to correlate respiratory and cardiac cycles with the movement of the tissue. Once the system has determined that it has successfully correlated the movement of the tissue within the required accuracy, it instructs the console to cease imaging, and it informs the operator that it is ready to begin the application of the radiation therapy.

The magnet is then moved into a storage location and the radiation therapy unit is moved into its radiation treatment location. When the operator invokes the radiation therapy from the system, the system controls the radiation therapy to position the radiation beam trajectory to the appropriate tissue given the current location within the respiratory and cardiac cycles. The system then continues to control the radiation therapy using the measurements from the respiratory and cardiac devices to move the beam in real-time to follow the tissue to be irradiated. When a pre-determined time (or equivalently, radiation dose) has completed, radiation stops, and the operator is informed that the treatment has completed successfully.

The system acts to monitor the respiratory and/or the cardiac cycles during radiation therapy beam application to ensure that the periodicity (that is the heart rate and respiration rate) has not changed outside of the bounds set for the needed accuracy of the movement of the beam. If the periodicity has changed by a sufficient degree, the radiation therapy beam is stopped until the respiratory and/or cardiac periodicity can locked onto again, and match the periodicity detected by the MR data.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A method for guiding radiation therapy of a patient comprising:
providing a treatment support for receiving and supporting the patient during treatment;
providing a radiation therapy treatment system for applying radiation therapy to the patient;
locating the treatment support and the radiation therapy treatment system in a radiation bunker arranged to prevent escape of the radiation;
providing a door on an opening into the bunker;
providing an MRI system for imaging the patient including a cylindrical magnet;
moving the radiation therapy treatment system in the bunker to a location spaced from the treatment support;
locating a patient on the treatment support in the bunker, the patient having a lesion requiring radiation therapy;
preparing the patient for radiation therapy on the treatment support;
with the radiation therapy treatment system moved to the spaced location, moving the cylindrical magnet from a position outside the bunker through the opening with the door open into a position surrounding the treatment support for obtaining images of the patient while on the treatment support;
the bunker, the door and the opening being shaped and arranged to allow the magnet to move into the bunker;
while the patient is on the treatment support, using the MRI system to obtain a series of images of a location of the lesion within the patient;
moving the magnet of the MRI system away from the treatment support and out of the bunker through the opening, and closing the door so as to allow the radiation therapy;
and during the radiation therapy, using the images of the patient to guide the radiation therapy.

2. The method according to claim 1 wherein the images from the MR system in an MR coordinate system are correlated relative to a coordinate system of the radiation therapy by using the treatment support as a common baseline.

3. The method according to claim 1 wherein the radiation therapy is generated by a collimated radiation source which is rotated round the lesion in a manner which controls the application of a required dose of radiation to the lesion while accommodating the shape of the lesion and the movement of the lesion.

4. The method according to claim 1 including, while the patient is on the treatment support during the obtaining of the images, obtaining data relating to respiration and/or heartbeat of the patient, using the series of images to generate lesion movement data relating to a correlation between movement of the location of the lesion and the data relating to the respiration and/or heartbeat and during the radiation therapy, using real time data relating to respiration and/or heartbeat of the patient and guiding the radiation therapy using the lesion movement data correlated to the real time data of the respiration and/or heartbeat.

5. The method according to claim 4 wherein the lesion movement data relating to a correlation between movement of the location of the lesion and the data relating to the respiration and/or heartbeat is obtained during a plurality of respiration cycles and cardiac cycles.

6. The method according to claim 4 wherein the MRI system acts to generate the series of images at a selected respiration rate and during the radiation therapy to monitor a respiratory rate to ensure that the rate has not changed outside of a bounds set for the needed accuracy of movement of a beam and in the event that the rate deviates by a predetermined degree, the beam is stopped, until the rate returns to the selected rate.

7. The method according to claim 4 wherein the data relating to respiration and/or heartbeat of the patient is obtained by a sensor independent of the MRI system.

8. The method according to claim 4 wherein the data relating to respiration and/or heartbeat of the patient is obtained by a sensor responsive to movement of the chest of the patient.

* * * * *